US008608824B2

(12) United States Patent
Steiner et al.

(10) Patent No.: US 8,608,824 B2
(45) Date of Patent: Dec. 17, 2013

(54) INTEGRATED METHOD FOR PRODUCING CARBONYL IRON POWDER AND HYDROCARBONS

(75) Inventors: Jochen Steiner, Bensheim (DE); Ekkehard Schwab, Neustadt (DE); Andreas Keller, Speyer (DE); Otto Watzenberger, Mannheim (DE); Ulrich Gräβle, Böhl-Iggelheim (DE); Manfred Julius, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 222 days.

(21) Appl. No.: 13/063,321

(22) PCT Filed: Sep. 2, 2009

(86) PCT No.: PCT/EP2009/061343
§ 371 (c)(1),
(2), (4) Date: Mar. 10, 2011

(87) PCT Pub. No.: WO2010/028995
PCT Pub. Date: Mar. 18, 2010

(65) Prior Publication Data
US 2011/0162484 A1 Jul. 7, 2011

(30) Foreign Application Priority Data
Sep. 10, 2008 (EP) ..................... 08164085

(51) Int. Cl.
*B22F 9/30* (2006.01)
*C07C 1/00* (2006.01)
(52) U.S. Cl.
USPC ............. 75/362; 266/138; 266/156; 208/423; 585/504; 585/531; 518/719

(58) Field of Classification Search
None
See application file for complete search history.

(56) References Cited

U.S. PATENT DOCUMENTS

| 4,459,369 A * | 7/1984 | Passariello ................. 502/306 |
| 4,532,229 A * | 7/1985 | Fiato et al. ................. 502/330 |
| 4,544,674 A | 10/1985 | Fiato et al. |
| 4,604,375 A * | 8/1986 | Soled et al. ................. 502/241 |
| 4,624,967 A * | 11/1986 | Fiato et al. ................. 518/700 |
| 4,788,222 A * | 11/1988 | Rice et al. ................. 518/700 |
| 5,026,403 A | 6/1991 | Michel-Kim |
| 5,118,715 A | 6/1992 | Iglesia et al. |
| 2008/0202123 A1 | 8/2008 | Sullivan et al. |
| 2009/0152499 A1 | 6/2009 | Bartenbach et al. |

(Continued)

FOREIGN PATENT DOCUMENTS

DE 528463 C 6/1931
DE 2919921 A1 11/1980

(Continued)

*Primary Examiner* — George Wyszomierski
(74) *Attorney, Agent, or Firm* — Novak Druce Connolly Bove + Quigg LLP

(57) ABSTRACT

Integrated process, in which pure carbonyl iron powder (CIP) is prepared by decomposition of pure iron pentacarbonyl (IPC) in a plant A, carbon monoxide (CO) liberated in the decomposition of the IPC is used in plant A for the preparation of further CIP from iron or is fed to an associated plant B for the preparation of synthesis gas or is fed to an associated plant C for the preparation of hydrocarbons from synthesis gas, and the CIP prepared in plant A is used as catalyst or catalyst component in an associated plant C for the preparation of hydrocarbons from synthesis gas from plant B.

11 Claims, 4 Drawing Sheets

(56) References Cited

U.S. PATENT DOCUMENTS

| | | |
|---|---|---|
| 2009/0186952 A1* | 7/2009 | Steynberg et al. ............ 518/704 |
| 2011/0112203 A1 | 5/2011 | Steiner et al. |
| 2011/0112204 A1 | 5/2011 | Steiner et al. |
| 2011/0112205 A1 | 5/2011 | Steiner et al. |
| 2011/0118365 A1 | 5/2011 | Steiner et al. |

FOREIGN PATENT DOCUMENTS

| | | | |
|---|---|---|---|
| EP | 0136255 | A2 | 4/1985 |
| FR | 2391978 | A1 | 12/1978 |
| GB | 2050859 | A | 1/1981 |
| JP | 03-164435 | A | 7/1991 |
| WO | WO-2006/127261 | A1 | 11/2006 |
| WO | WO-2008/083600 | A1 | 7/2008 |
| WO | WO 2009/071463 | | 6/2009 |
| WO | WO 2010/028995 | | 3/2010 |
| WO | WO 2011/054734 | | 3/2011 |
| WO | WO 2011/054735 | | 3/2011 |
| WO | WO 2011/054738 | | 3/2011 |

\* cited by examiner

INTEGRATED METHOD FOR PRODUCING CARBONYL IRON POWDER AND HYDROCARBONS

CROSS-REFERENCE TO RELATED APPLICATIONS

This application is a national stage application (under 35 U.S.C. § 371) of PCT/EP2009/061343, filed Sep. 2, 2009, which claims benefit of European application 08164085.6, filed Sep. 10, 2008. The contents of each of these references are incorporated herein by reference in their entireties.

FIELD OF THE INVENTION

The present invention relates to an integrated process for the preparation of pure carbonyl iron powder (CIP) by decomposition of pure iron pentacarbonyl (IPC) and of hydrocarbons from synthesis gas.

BACKGROUND

The preparation of pure carbonyl iron powder (CIP) by decomposition of pure iron pentacarbonyl (IPC) is known, for example, from Ullmann's Encyclopedia of Industrial Chemistry, Iron Compounds, E. Wildermuth, H. Stark et al., published online: 15 Jun. 2000, (Wiley-VCH-Verlag).

For this purpose, iron particles are reacted under high pressure and at high temperatures to form iron pentacarbonyl (IPC, $Fe(CO)_5$). The impurities present in the iron are preferably partly removed by distillation at the carbonyl stage and highly pure IPC is obtained. This compound is the precursor for the decomposition of the IPC into CIP in the subsequent step. In this step, the IPC is decomposed to CIP at high temperatures, e.g. in a downflow decomposer.

In downstream process steps, this primary CIP can be processed to produce a catalyst for the Fischer-Tropsch synthesis. The further processing and the suitability of the catalyst for the preparation of hydrocarbons, in particular lower olefins, from synthesis gas (Fischer-Tropsch synthesis) is described in the patent applications EP 07112853.2 of Jul. 20, 2007 and EP 08156965.9 of May 27, 2008 (both BASF AG or SE).

It is known that hydrocarbons can be prepared from carbon monoxide (CO) and hydrogen ($H_2$) over metal catalysts, e.g. iron or cobalt catalysts.

Further iron catalysts for the Fischer-Tropsch synthesis are described in WO 2006/127261 A1, page 2, section [005] (precipitated catalysts) and loc. cit. section [006] (fused catalysts).

The main disadvantages in the preparation of iron Fischer-Tropsch catalysts or of precipitated catalysts in general are the energy—and labor—intensive preparation and the waste materials obtained, which usually have to be classified as environmentally harmful materials.

BRIEF SUMMARY

It is an object of the present invention to overcome disadvantages of the prior art and discover an improved economical process for the preparation of pure carbonyl iron powder (CIP) and of hydrocarbons. The first-named process should, in particular, avoid the large molar amounts of waste products obtained in conventional catalyst production. Salt burdens and washing water in particular represent production factors which require complicated after-treatment and may have to be disposed of at high cost. The second process should make it possible to obtain short-chain hydrocarbons from synthesis gas. In a particular embodiment, the process should preferably give C2-C8-olefins (C2- to C8-olefins), in particular C2-C4-olefins (C2- to C4-olefins), in particular ethene, propene and 1-butene, with a very small amount of methane, carbon dioxide, alkanes (e.g. C2-C4-alkanes) and higher hydrocarbons, i.e. hydrocarbons having five or more carbon atoms (C5+ fractions) being obtained at the same time.

According to the invention, it was recognized, inter alia, that:

If the mass circuit of carbon monoxide (CO) is considered, the preparation of IPC and the subsequent decomposition into CIP can be considered to be a circular process in which recycling of the CO takes place. Compared to alternative preparative methods, e.g. precipitation of iron compounds, calcination and subsequent reduction to metallic iron, the route via the carbonyl compound is especially advantageous in that no waste materials (such as salts) and wastewater are obtained. An integrated process in which energy and mass circuits are coupled in such a way that an iron-based catalyst for chemical reactions, in particular for the Fischer-Tropsch synthesis, is prepared from iron or iron oxide as raw material via the intermediate stage of carbonyl iron powder (CIP) would be advantageous.

DETAILED DESCRIPTION OF THE PREFERRED EMBODIMENTS

Figure 1:
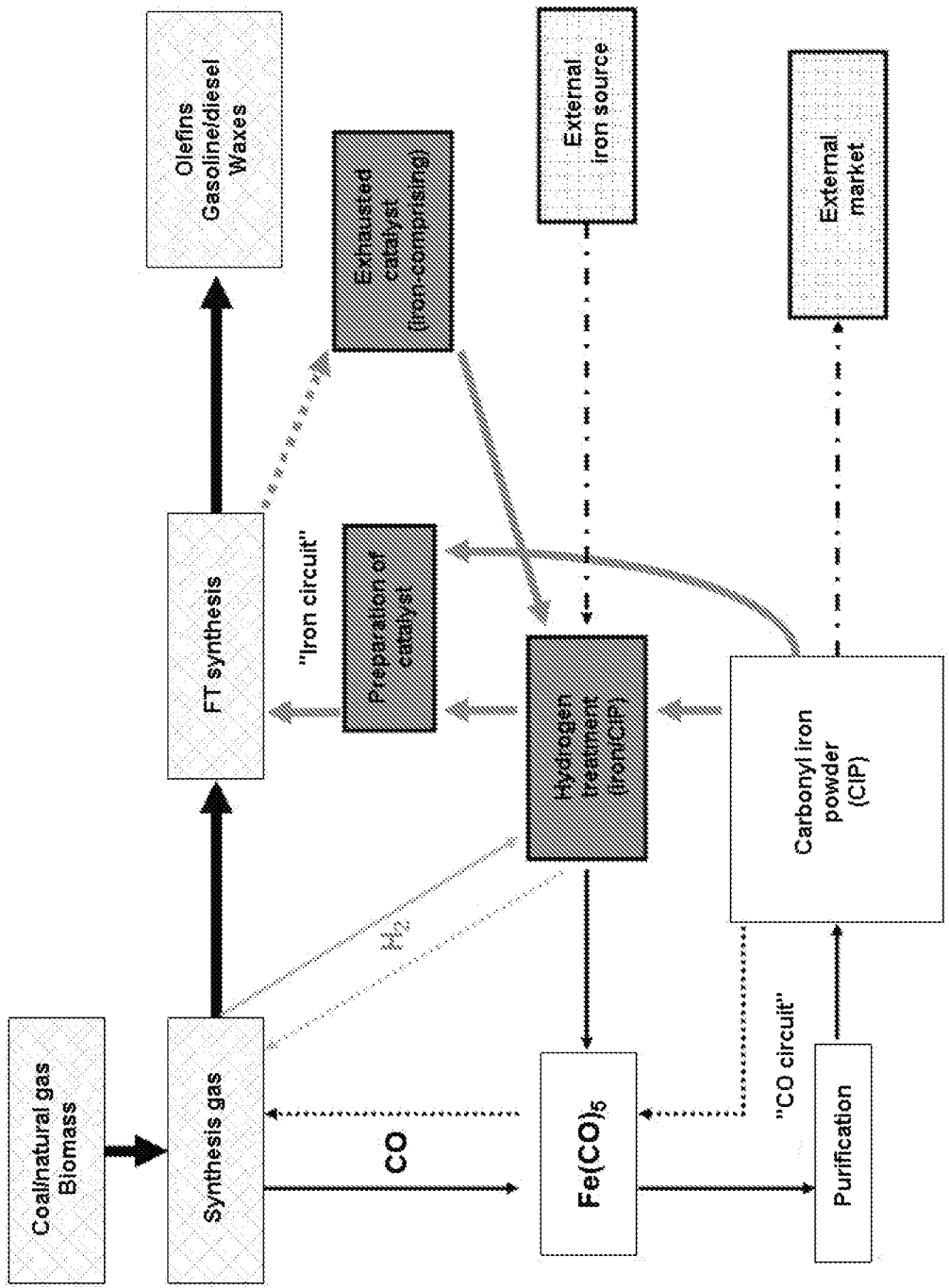
FIG. 1 is a schematic depiction of preferred embodiments of the integrated process of the invention.

We have accordingly found an integrated process in which pure carbonyl iron powder (CIP) is prepared by decomposition of pure iron pentacarbonyl (IPC) in a plant A, carbon monoxide (CO) liberated in the decomposition of the IPC is used in plant A for the preparation of further CIP from iron or is fed to an associated plant B for the preparation of synthesis gas or is fed to an associated plant C for the preparation of hydrocarbons from synthesis gas, and the CIP prepared in plant A is used as catalyst or catalyst component in an associated plant C for the preparation of hydrocarbons from synthesis gas from plant B.

Regarding the process for the preparation of pure CIP in plant A:

The decomposition of IPC is preferably a thermal decomposition of gaseous IPC.

The CIP obtained after the decomposition of IPC is preferably treated with hydrogen before being used further.

This treatment of the CIP with hydrogen is preferably carried out at a temperature in the range from 300 to 600° C.

This treatment reduces the residual content of carbon, nitrogen and also oxygen in the CIP. (DE 528 463 C1, 1927).

The hydrogen used preferably comes from an associated plant B for the preparation of synthesis gas.

The iron used for the preparation of CIP is preferably treated beforehand with hydrogen.

This treatment of the iron with hydrogen is preferably carried out at a temperature in the range from 300 to 1000° C.

This treatment reduces, in particular, the oxygen content of the iron.

The hydrogen used preferably comes from an associated plant B for the preparation of synthesis gas.

The IPC used for the preparation of pure CIP is preferably purified beforehand by distillation.

This distillation removes impurities such as transition metals, in particular Ni and Cr, in the form of their carbonyl compounds.

Additional CO required for the preparation of further IPC preferably comes from an associated plant B for the preparation of synthesis gas.

The pure carbonyl iron powder (CIP) prepared according to the process in plant A preferably has the following characteristics:

The CIP comprises spherical primary particles whose diameter is preferably in the range from ≥1 to 50 µm. The primary particles can be agglomerated.

Regarding the process in plants B and C for the preparation of hydrocarbons by reaction of carbon monoxide with hydrogen (i.e. of synthesis gas):

The synthesis gas required is preferably prepared in plant B by generally known methods (as described, for example, in Weissermel et al., Industrial Organic Chemistry, Wiley-VCH, Weinheim, 2003, pages 15 to 24), for example by reaction of coal or methane with steam or by partial oxidation of methane. Suitable primary energy carriers for the preparation of synthesis gas are coal and natural gas and also biomass.

The synthesis gas preferably has a molar ratio of carbon monoxide to hydrogen in the range from 3:1 to 1:3. In plant C, particular preference is given to using a synthesis gas which has a molar mixing ratio of carbon monoxide to hydrogen in the range from 2:1 to 1:2.

In a particular embodiment of the integrated process of the invention, the synthesis gas comprises carbon dioxide ($CO_2$). The $CO_2$ content is preferably in the range from 1 to 50% by weight.

In a particular embodiment, the synthesis gas is prepared by gasification of coal in plant B. Such processes are, for example, also described in Nexant Inc./Chem Systems PERP 03/04-S4—Developments in Syngas Technology, 2005, pages 10/11 and 58-63.

The synthesis gases which can be prepared by gasification of coal have a molar ratio of carbon monoxide to hydrogen in the range from 2.36 to 0.4, particularly preferably in the range from 2 to 0.6, in particular in the range from 1.5 to 0.8.

Exhausted catalyst obtained in the process for the preparation of hydrocarbons in plant C is, preferably after treatment with hydrogen as described above, preferably used as additional iron source for the preparation of carbonyl iron powder (CIP) in plant A.

According to the invention, the preparation of CIP in plant A for use as catalyst or catalyst component in an associated plant C for the preparation of hydrocarbons combined with a CO recycling process with integration of a plant B for the preparation of synthesis gas and coupling to an iron circuit by recirculation of the exhausted catalyst from plant C to plant A is particularly advantageous.

Preferred embodiments of the integrated process according to the invention are shown schematically in FIG. 1.

Individual steps in FIG. 1 can be described as follows as a preferred embodiment, starting from "consumed catalyst (iron-comprising)":

1) Iron oxide is mixed with iron (Fe) or iron oxide (the latter two in each case coming from exhausted catalyst from plant C) and reduced. The hydrogen for reduction comes from the synthesis gas plant B. Unconsumed hydrogen can be fed back into the synthesis gas plant B or fed directly to the Fischer-Tropsch plant C for the preparation of hydrocarbons.

2) The metallic iron obtained is reacted with CO from the synthesis gas plant B in plant A to form IPC.

3) The IPC is decomposed into CIP in plant A and the CO liberated is fed to the synthesis gas plant B, the Fischer-Tropsch plant C or back to the IPC synthesis in plant A. The last-named alternative corresponds to direct CO recycling.

4) The CIP from plant A is processed in subsequent steps to give the iron Fischer-Tropsch catalyst and used in the Fischer-Tropsch plant C for the synthesis of hydrocarbons. In addition, the CIP can be marketed externally.

5) The catalyst removed from plant C is fed back to IPC production via the "catalyst circuit" of the synthesis of metallic iron (step 1).

Owing to the coupling according to the invention of the individual process steps, virtually closed mass circuits are preferably obtained both for the carbon monoxide used and for the iron. The resulting integrated process thus makes environmentally friendly and resource-conserving production of iron-based catalysts possible.

Further description of the process in plant C for the preparation of hydrocarbons by reaction of synthesis gas:

A carbonyl iron powder (CIP) having spherical primary particles is preferably used in the process in plant C for the preparation of hydrocarbons, preferably olefins, by reaction of carbon monoxide with hydrogen in the presence of a heterogeneous CIP-comprising catalyst.

The proportion of spherical primary particles in the carbonyl iron powder is preferably >90% by weight, particularly preferably >95% by weight, very particularly preferably >98% by weight.

The spherical primary particles preferably have a diameter in the range from 0.01 to 250 µm, especially in the range from 0.1 to 200 µm, very especially in the range from 0.5 to 150 µm, more particularly in the range from 0.7 to 100 µm, more particularly in the range from 1 to 70 µm, particularly preferably in the range from 1.5 to 50 µm.

The iron content of the spherical primary particles is preferably >97% by weight, particularly preferably 99% by weight, in particular 99.5% by weight, in each case calculated without any promoters present.

The spherical primary particles are preferably free of pores.

In particular, the preferred carbonyl iron powder does not comprise any thread-like primary particles, in particular not the iron whiskers disclosed in DE 29 19 921 A1 and "Fachberichte für Oberflächentechnik", July/August 1970, pages 145 to 150, in addition to the spherical primary particles.

Figure 2:
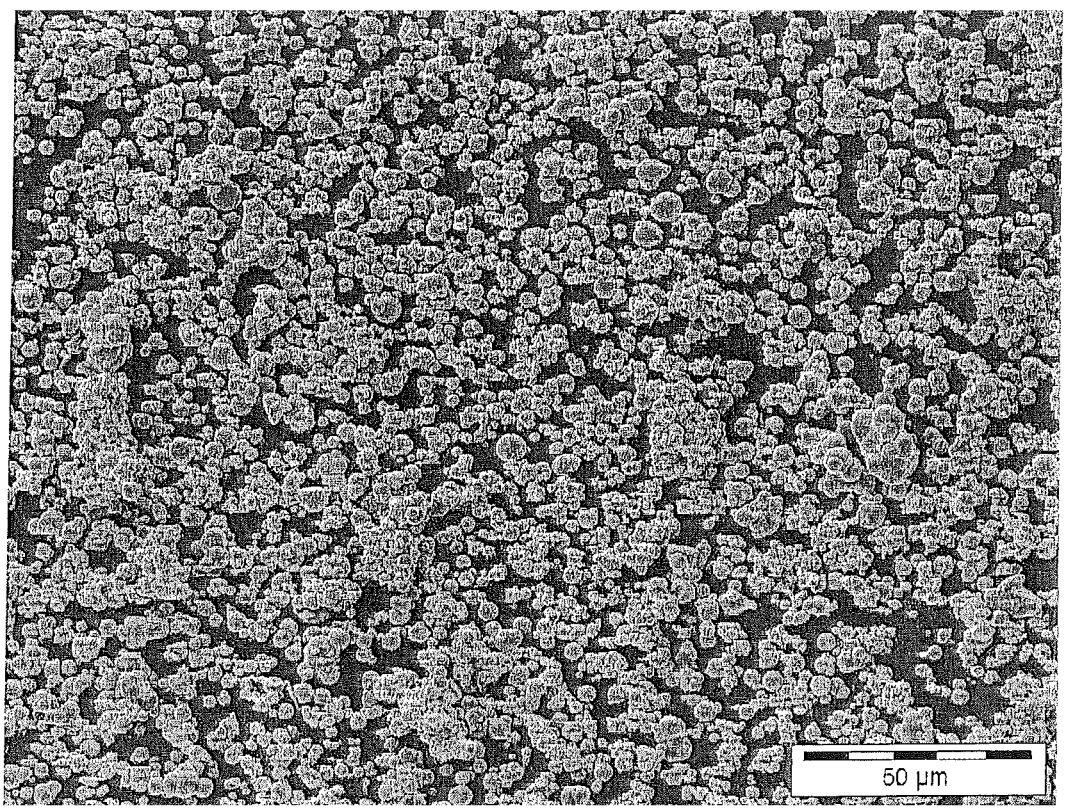
FIGS. 2-4 show scanning electron micrographs of preferably used carbonyl iron powder having spherical primary particles.
Figure 3:
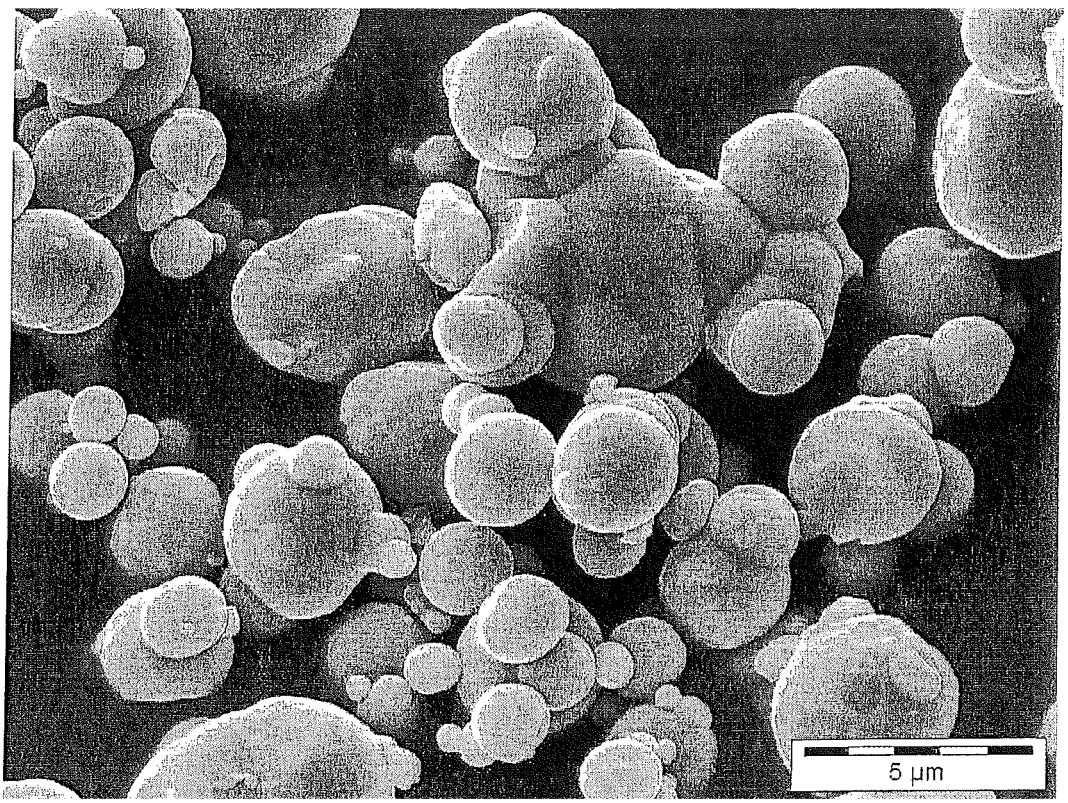
Figure 4:
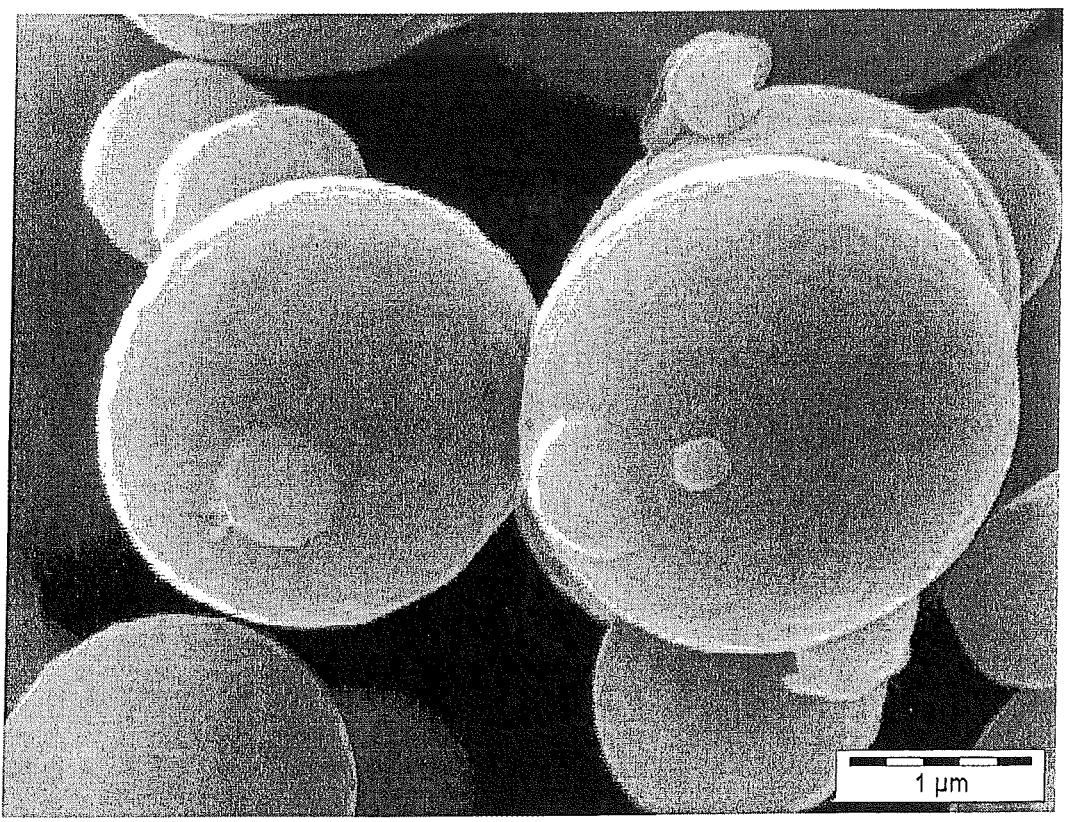

FIGS. 2 to 4 show scanning electron micrographs of preferably used carbonyl iron powder having spherical primary particles.

Carbonyl iron powder having spherical primary particles which can be used in the process can be obtained, for example, under the name "Carbonyleisenpulver CN" from BASF AG, now BASF SE, D-67056 Ludwigshafen.

The carbonyl iron powder, in particular carbonyl iron powder having spherical primary particles, is obtained by thermal decomposition of gaseous iron pentacarbonyl (IPC, $Fe[CO]_5$) which has, in particular, been purified beforehand by distillation.

The spherical primary particles can be partly, e.g. to an extent of 25-95% by weight, agglomerated.

The product obtained in this way is preferably after-treated by reduction with hydrogen.

Even without any additives, the carbonyl iron powder displays an advantageous catalytic activity.

The carbonyl iron powder can be doped with a promoter or a plurality of promoters to increase the catalytic activity.

Promoters in iron catalysts for Fischer-Tropsch syntheses are described, for example, in M. Janardanarao, Ind. Eng.

Chem. Res. 1990, 29, pages 1735 to 1753, or C. D. Frohning et al. in "Chemierohstoffe aus Kohle", 1977, pages 219 to 299. As suitable promoters, the catalysts can comprise, for example, one or more of the elements vanadium, copper, nickel, cobalt, manganese, chromium, zinc, silver, gold, potassium, calcium, sodium, lithium, cesium, platinum, palladium, ruthenium, sulfur, chlorine, in each case in elemental form or in ionic form.

The total doping of the carbonyl iron powder (i.e. the sum of promoters if a plurality of promoters is present) is preferably in the range from 0.01 to 30% by weight, particularly preferably from 0.01 to 20% by weight, very particularly preferably from 0.1 to 15% by weight, e.g. from 0.2 to 10% by weight, in particular from 0.3 to 8% by weight, in each case based on iron.

In a particular embodiment of the process, the carbonyl iron powder is doped with potassium ions and/or sodium ions as promoter.

In one embodiment, the carbonyl iron powder is particularly preferably doped with a total of from 0.01 to 10% by weight, preferably from 0.1 to 5% by weight, of potassium ions and/or sodium ions (in each case based on iron).

The application of the promoters mentioned can be effected, for example, by impregnation of the carbonyl iron powder with aqueous salt solutions of the metals mentioned, preferably carbonates, chlorides, nitrates or oxides.

Furthermore, the elements acting as promoter can also be applied by thermal decomposition of the corresponding gaseous carbonyl compounds, e.g. copper, cobalt or nickel carbonyls, during preparation of the carbonyl iron powder.

The carbonyl iron powder can, in a further embodiment of the catalyst, be applied to support materials. Preferred support materials are $TiO_2$, $SiO_2$, $Al_2O_3$, zeolites, carbon (C).

In the process for the preparation of hydrocarbons, in particular olefins, the optionally doped and optionally supported carbonyl iron powder can be used in the form of pellets.

The pellets are obtained by methods known to those skilled in the art. Preferred shapes of the pellets are tablets and rings.

The pellets can also be comminuted again, e.g. by milling, before being used in the process.

The catalysts can be converted into a more synthesis-active state by treatment with hydrogen and/or carbon monoxide at elevated temperature, in particular at temperatures above 300° C., before being used in the process. However, this additional activation is not absolutely necessary.

The process for the preparation of hydrocarbons, in particular olefins, is preferably carried out at a temperature in the range from 200 to 500° C., particularly preferably from 300 to 400° C.

The absolute pressure is preferably in the range from 1 to 100 bar, particularly preferably from 5 to 50 bar.

The GHSV (gas hourly space velocity) is preferably in the range form 100 to 10,000, particularly preferably from 300 to 5000, parts by volume of feed stream per part by volume of catalyst and hour (l/l·h).

Preferred reactors for carrying out the process of the invention are: Fluidized-bed reactor, fixed-bed reactor, suspension reactor.

In a fluidized-bed or suspension reactor, the catalyst is preferably used in powder form. The powder can be the primary particles of the carbonyl iron powder or else agglomerates thereof.

The powder can also be obtained by milling previously produced pellets.

In a fixed-bed reactor, the catalyst is used as shaped bodies, preferably in the form of pellets.

The use of such reactors for the Fischer-Tropsch synthesis is, for example, described in C. D. Frohning et al. in "Chemierohstoffe aus Kohle", 1977, pages 219 to 299, or B. H. Davis, Topics in Catalysis, 2005, 32 (3-4), pages 143 to 168.

C2-C8-Olefins, in particular C2-C4-olefins, especially ethene, propene and 1-butene, are preferably prepared as hydrocarbons in plant C.

The process for the preparation of, in particular, olefins gives a product mixture comprising olefins with an olefin carbon selectivity, in particular an α-olefin carbon selectivity, for the C2-C4 range of preferably at least 30%, e.g. in the range from 30 to 45%. Carbon dioxide formed is not taken into account in the calculation of the selectivity (i.e. excluding $CO_2$).

In a particularly preferred embodiment, a product mixture comprising olefins is obtained with an olefin carbon selectivity for the C2-C4 range of at least 30%, where at least 90% of this at least 30% is in turn made up of ethene, propene, 1-butene. Carbon dioxide formed is not taken into account in the calculation of the selectivity (i.e. excluding $CO_2$).

In a particularly preferred embodiment, a product mixture comprising olefins is obtained with an olefin carbon selectivity for the C2-C4 range of at least 40%, e.g. in the range from 40 to 45%, where at least 90% of this at least 40% is in turn made up of ethene, propene, 1-butene. Carbon dioxide formed is not taken into account in the calculation of the selectivity (i.e. excluding $CO_2$).

The olefins obtained are used, for example, in processes for the preparation of polyolefins, epoxides, oxo products, acrylonitriles, acrolein, styrene. See also: Weissermel et al., Industrial Organic Chemistry, Wiley-VCH, Weinheim, 2003, pages 145 to 192 and 267 to 312.

FIG. 1:

Schematic depiction of preferred embodiments of the integrated process of the invention [integrated facility comprising synthesis gas plant (B), Fischer-Tropsch plant (C), CIP plant (A)].

FIGS. 2 to 4:

Carbonyl iron powder (CIP) having spherical primary particles which is preferably used in the process for the preparation of hydrocarbons, in particular olefins, in plant C.

The invention claimed is:

1. An integrated process, wherein pure carbonyl iron powder (CIP) is prepared by decomposition of pure iron pentacarbonyl (IPC) in a plant A, carbon monoxide (CO) liberated in the decomposition of the IPC is used in plant A for the preparation of further IPC from iron or is fed to an associated plant B in which synthesis gas is prepared or is fed to an associated plant C in which hydrocarbons are prepared from synthesis gas, the CIP prepared in plant A is used as catalyst or catalyst component in an associated plant C in which hydrocarbons are prepared from synthesis gas from plant B, exhausted catalyst obtained in plant C is used as additional iron source for the preparation of CIP in plant A and the CIP obtained in plant A after the decomposition of IPC is treated with hydrogen before being used further, where the hydrogen used comes from an associated plant B in which synthesis gas is prepared.

2. The process according to claim 1, wherein the treatment of the CIP with hydrogen is carried out at a temperature in the range from 300 to 600° C.

3. The process according to claim 1, wherein the iron used in plant A for the preparation of CIP is treated beforehand with hydrogen.

4. The process according to claim 3, wherein the treatment of the iron with hydrogen is carried out at a temperature in the range from 300 to 1000° C.

5. The process according to claim 4, wherein the hydrogen used comes from an associated plant B in which synthesis gas is prepared.

6. The process according to claim 3, wherein the hydrogen used comes from an associated plant B in which synthesis gas is prepared.

7. The process according to claim 1, wherein additional CO required in plant A for the preparation of further IPC comes from an associated plant B in which synthesis gas is prepared.

8. The process according to claim 1, wherein C2-C4-olefins are prepared as hydrocarbons in plant C.

9. The process according to claim 1, wherein the synthesis gas is prepared by gasification of coal in plant B.

10. The process according to claim 1, wherein the IPC used in plant A for the preparation of pure CIP is purified beforehand by distillation.

11. The process according to claim 1, wherein the decomposition of IPC in plant A is a thermal decomposition of gaseous IPC.

* * * * *